(12) United States Patent
Shiraishi et al.

(10) Patent No.: US 10,694,080 B2
(45) Date of Patent: Jun. 23, 2020

(54) ENDOSCOPE SYSTEM

(71) Applicant: OLYMPUS CORPORATION, Tokyo (JP)

(72) Inventors: Hiroshi Shiraishi, Hino (JP); Tomoki Iwasaki, Fuchu (JP); Kenji Yamazaki, Hino (JP); Susumu Hashimoto, Hachioji (JP); Kyosuke Mizuno, Hino (JP); Yosuke Kujuuro, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/419,088

(22) Filed: May 22, 2019

(65) Prior Publication Data

US 2019/0273846 A1 Sep. 5, 2019

Related U.S. Application Data

(63) Continuation of application No. PCT/JP2017/033718, filed on Sep. 19, 2017.

(30) Foreign Application Priority Data

Nov. 25, 2016 (JP) .................. 2016-228649

(51) Int. Cl.
*A61B 1/00* (2006.01)
*A61B 1/045* (2006.01)
(Continued)

(52) U.S. Cl.
CPC ......... *H04N 5/2173* (2013.01); *A61B 1/0002* (2013.01); *A61B 1/00009* (2013.01); *A61B 1/045* (2013.01); *H04N 7/183* (2013.01)

(58) Field of Classification Search
None
See application file for complete search history.

(56) References Cited

U.S. PATENT DOCUMENTS 8,878,919 B2 11/2014 Tsuyuki
2006/0155166 A1\* 7/2006 Takahashi .............. A61B 1/045
600/109
(Continued)

FOREIGN PATENT DOCUMENTS

JP 2009-213742 A 9/2009
JP 2013-078591 A 5/2013
WO WO 2013/061819 A1 5/2013

OTHER PUBLICATIONS

International Search Report dated Dec. 26, 2017 issued in PCT/JP2017/033718.

*Primary Examiner* — Fernando Alcon
(74) *Attorney, Agent, or Firm* — Scully, Scott, Murphy & Presser, P.C.

(57) ABSTRACT

An endoscope system includes: an endoscope having an image sensor configured to image an inside of a subject; a processor configured to perform predetermined image processing on a video signal that is imaged by the image sensor; a storage that is provided in the endoscope, the storage being configured to store compressed data obtained by compressing data volume of first non-compressed data that is used for correction of an image imaged by the image sensor; a restoring circuit configured to read the compressed data from the storage to restore the compressed data to the first non-compressed data when data is transferred from the endoscope to the processor; and an image correcting circuit that is provided in the endoscope, the image correcting circuit being configured to correct the image imaged by the image sensor by using the first non-compressed data restored by the restoring circuit.

9 Claims, 4 Drawing Sheets

(51) Int. Cl.
*H04N 5/217* (2011.01)
*H04N 7/18* (2006.01)

(56) References Cited

U.S. PATENT DOCUMENTS

| | | | |
|---|---|---|---|
| 2009/0251532 A1* | 10/2009 | Abe | A61B 1/045 348/71 |
| 2010/0245551 A1* | 9/2010 | Morita | A61B 1/00009 348/68 |
| 2017/0034484 A1* | 2/2017 | Yanagidate | A61B 1/04 |
| 2019/0239725 A1* | 8/2019 | Ogasawara | A61B 1/00163 |
| 2019/0239731 A1* | 8/2019 | Hanzawa | G02B 21/36 |

* cited by examiner

1

ENDOSCOPE SYSTEM

CROSS-REFERENCE TO RELATED APPLICATION

This application is a continuation of PCT International Application No. PCT/JP2017/033718 filed on Sep. 19, 2017, which designates the United States, incorporated herein by reference, and which claims the benefit of priority from Japanese Patent Application No. 2016-228649, filed on Nov. 25, 2016, incorporated herein by reference.

BACKGROUND

1. Technical Field

The present disclosure relates to an endoscope system.

2. Related Art

In the medical field, endoscope systems have been used when observing an organ of a subject, such as a patient. An endoscope system includes an endoscope, which is an imaging apparatus that is inserted into a body of a subject, and that images the inside of the subject to output a video signal, and a processor that performs predetermined image processing on the video signal output by the endoscope.

In the endoscope system, when the endoscope is connected to the processor, information specific to the endoscope is transferred from the endoscope to the processor. For example, in JP-A-2009-213742, a configuration of transferring scope identification information from a read-only memory (ROM) of an endoscope to a central processing unit (CPU) of a processor device is disclosed.

SUMMARY

In some embodiments, an endoscope system includes: an endoscope having an image sensor configured to image an inside of a subject; a processor configured to perform predetermined image processing on a video signal that is imaged by the image sensor; a storage that is provided in the endoscope, the storage being configured to store compressed data obtained by compressing data volume of first non-compressed data that is used for correction of an image imaged by the image sensor; a restoring circuit configured to read the compressed data from the storage to restore the compressed data to the first non-compressed data when data is transferred from the endoscope to the processor; and an image correcting circuit that is provided in the endoscope, the image correcting circuit being configured to correct the image imaged by the image sensor by using the first non-compressed data restored by the restoring circuit.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, embodiments of an imaging system and an imaging apparatus according to the disclosure are described with reference to the drawings. The embodiments are not intended to limit the disclosure. In the following embodiments, an endoscope system and an endoscope are described as an example, but the disclosure is applicable to general imaging systems and imaging apparatus.

Moreover, like reference symbols are given to identical or corresponding components throughout the drawings. Furthermore, it is noted that the drawings are of schematic illustration, and a relationship in dimensions of respective components, a ratio of the respective components, and the like may differ from those in an actual situation. There can be part in which relationships in dimensions or ratios differ from one another among the drawings also.

Embodiment

Figure 1:
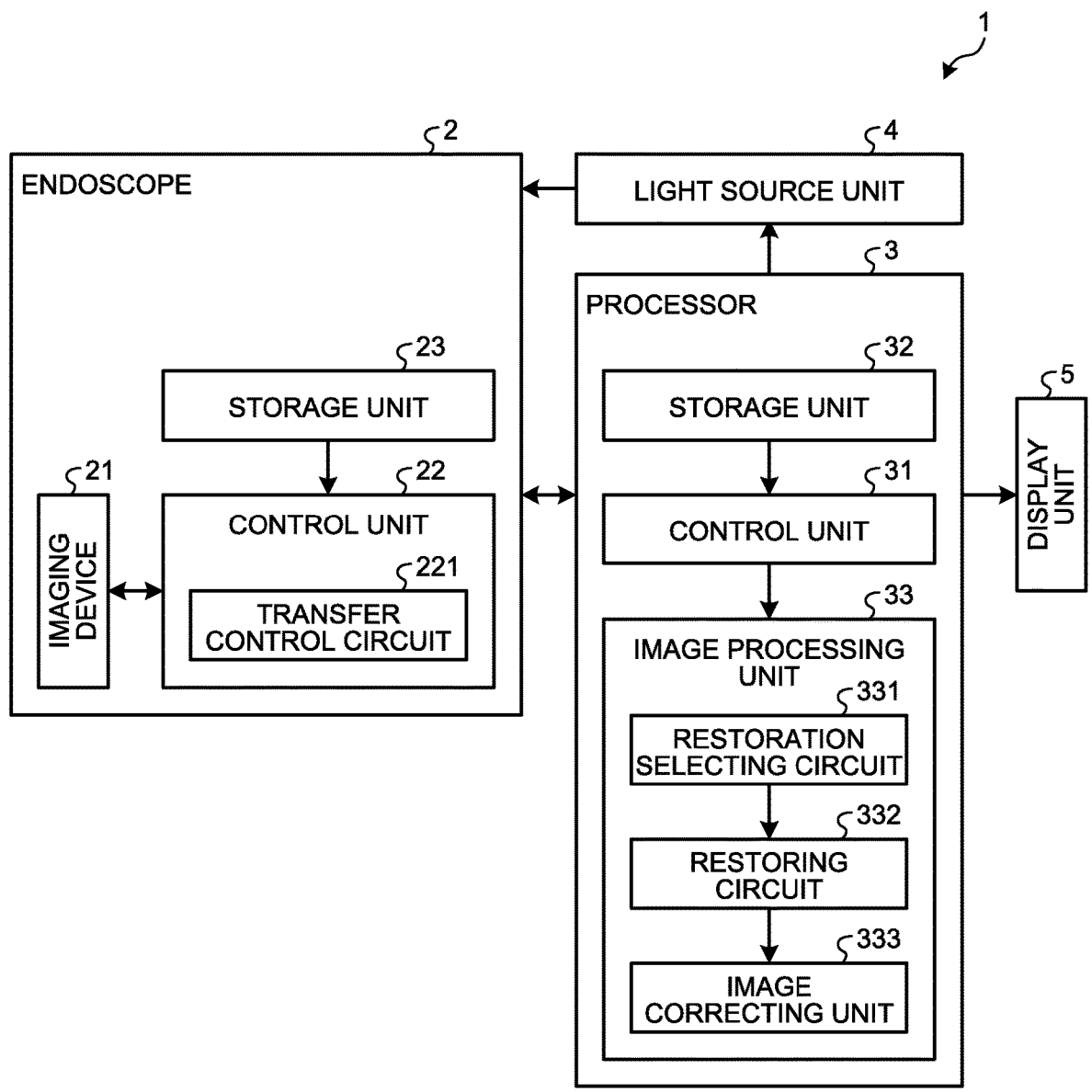
FIG. 1 is a schematic diagram illustrating a configuration of an endoscope system according to an embodiment of the disclosure.

FIG. 1 is a schematic diagram illustrating a configuration of an endoscope system according to an embodiment of the disclosure. As illustrated in FIG. 1, an endoscope system 1 as an imaging system according to the embodiment includes an endoscope 2 as an imaging apparatus, a processor 3, a light source unit 4, and a display unit 5.

Configuration of Endoscope

The endoscope 2 has a flexible distal end portion to be inserted into a body cavity of a subject to image the subject to be observed, and outputs a video signal. The endoscope 2 includes an imaging device 21 that images the subject and outputs a video signal, a control unit 22 that drives the imaging device 21 according to a control by the processor 3, and a storage unit 23 that stores identification information of the endoscope 2 and the like.

The imaging device 21 is constituted of, for example, a charge-coupled device (CCD) image sensor, or a complementary metal oxide semiconductor (CMOS) image sensor. The imaging device 21 receives light collected by an objective optical system not shown, photoelectric-converts the light into an electrical signal, subjects the signal to predetermined signal processing, and outputs a digital video signal thus obtained.

The control unit 22 is constitute of a general-purpose processor, such as a CPU, or a dedicated processor including various kinds of arithmetic circuit having a specific function, such as an application specific integrated circuit (ASIC) and a field programmable gate array (FPGA). The control unit 22 controls the imaging device 21 according to a signal that is output from the processor 3, to control imaging by the imaging device 21. The control unit 22 includes a transfer control circuit 221 that determines a type of the processor 3 to which the endoscope 2 is connected, and that controls transfer of compressed data to the processor 3 described later. Specifically, the transfer control circuit 221 transfers compressed data to the processor 3 when the processor 3 to which the endoscope 2 is connected is of a type capable of performing image processing with compressed data, and suspends transfer of compressed data to the processor 3 when the processor 3 to which the endoscope 2 is connected is of a type not capable of performing image processing with compressed data. The control unit 22 may be constituted of a dedicated device in which a CPU and an FPGA is combined, and may have a double monitoring configuration by equipping the dedicated device with an integrated watchdog timer to detect an error in a program in the device, and by using an integrated circuit (IC) for monitoring the watchdog timer outside the dedicated device when monitoring a runaway of the program. Specifically, reset monitoring time of the IC for monitoring the watchdog timer provided outside is set to be longer than reset and/or restart time of the integrated watchdog timer.

The storage unit 23 is implemented by a ROM, a random access memory (RAM), or the like. The storage unit 23 is provided inside the endoscope 2 including the imaging device 21. The storage unit 23 stores identification information of the endoscope 2, and stores data that is used for correction of an image imaged by the imaging device 21.

Figure 2:
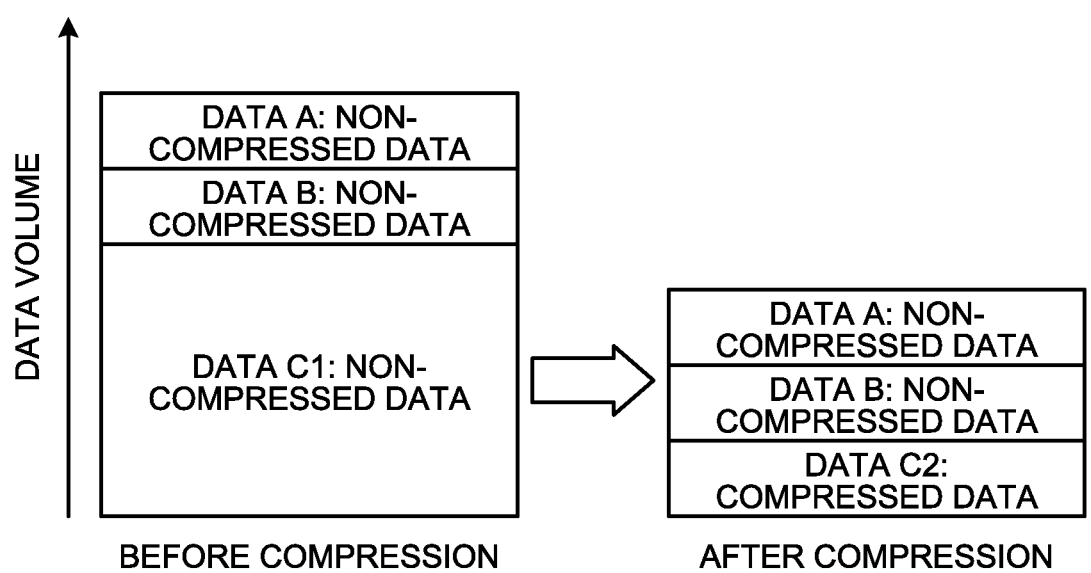
FIG. 2 is a diagram for describing data stored in a storage unit illustrated in FIG. 1.

FIG. 2 is a diagram for describing data stored in the storage unit 23 illustrated in FIG. 1. As illustrated in FIG. 2, the storage unit 23 stores data A and data B as non-compressed data (second non-compressed data), out of data A, B, C1 that are non-compressed data to be used for correction of an image imaged by the imaging device 21. Furthermore, the storage unit 23 stores data C2 that is compressed data obtained by compressing data volume of data C1, which is non-compressed data (first non-compressed data). A data compression format is not limited to a particular format, but by storing a relative value or a difference value calculated from a value corresponding to each pixel of data C1 in the storage unit 23, the data volume can be compressed. Alternatively, data compressed by subjecting data C1 to Huffman coding may be stored in the storage unit 23 as data C2.

The non-compressed data (data A and data B) is a parameter, for example, used for white defect correction or black defect correction.

Data C1, which is non-compressed data, is a parameter used when different correction is performed per pixel with respect to all pixels of an image imaged by the imaging device 21. Specifically, data C1 is a parameter to correct variations in sensitivity per pixel of the imaging device 21 originating in a color filter in the Bayer arrangement, or in sensitivity of each pixel of the imaging device 21. Note that by compressing data C1 that is a parameter varying per pixel, and is large-volume data as illustrated in FIG. 2, the entire data volume can be effectively compressed.

Configuration of Processor

The processor 3 illustrated in FIG. 1 subjects a video signal output from the endoscope 2 to predetermined image processing to output an image signal, and generally controls an action of the entire endoscope system 1. The processor 3 includes a control unit 31 that controls an action of the entire endoscope system 1, a storage unit 32 that stores a video signal output by the endoscope 2, and an image processing unit 33 that performs predetermined image processing on the video signal output by the endoscope 2.

The control unit 31 is constituted of a general-purpose processor, such as a CPU, or a dedicated processor including various kinds of arithmetic circuit, such as an ASIC and an FPGA. The control unit 31 performs drive control of the respective components, input and output of information with respect to the respective components, and the like. Moreover, the control unit 31 controls imaging of the imaging device 21 of the endoscope 2.

The storage unit 32 stores various kinds of programs including an actuation program to perform an actuation method of the endoscope 2. The actuation program can also be distributed widely, recorded in a computer-readable recording medium, such as a hard disk, a flash memory, a CD-ROM, a digital versatile disk (DVD)-ROM, and a flexible disk. The various kinds of programs described above can also be acquired by downloading the programs through a communication network. The communication network herein is implemented by, for example, an existing public network, a local area network (LAN), or a wide area network (WAN), regardless of wired or wireless network.

The storage unit 32 having the configuration as described above is implemented by using a ROM in which various kinds of programs and the like are installed in advance, a RAM that stores arithmetic parameters and data of various processing, and the like.

The image processing unit 33 is constituted of a general-purpose processor, such as an CPU, or a dedicated processor including various kinds of arithmetic circuits that perform specific functions, such as an ASIC and an FPGA. The image processing unit 33 performs image processing, such as synchronization processing, white balance (WB) adjustment processing, gain adjustment processing, gamma correction processing, and digital/analog (D/A) conversion processing, with respect to a digital video signal to convert into an image signal, and outputs the image signal.

The image processing unit 33 includes a restoration selecting circuit 331, a restoring circuit 332, an image correcting unit 333.

The restoration selecting circuit 331 reads data C2, which is compressed data, and data A and data B, which are non-compressed data, from the storage unit 23, and outputs data C2, which is compressed data, selectively to the restoring circuit 332.

The restoring circuit 332 reads data C2, which is compressed data, from the storage unit 23 through the restoration selecting circuit 331, and restores data C2, which is compressed data, to data C1, which is non-compressed data. Specifically, the restoring circuit 332 restores compressed data that are is a relative value or a difference value calculated from a value corresponding to each pixel, for example, to an absolute value corresponding to each pixel.

The image correcting unit 333 corrects an image imaged by the imaging device 21 by using data C1, which is non-compressed data restored by the restoring circuit 332. Specifically, the image correcting unit 333 corrects an image imaged by the imaging device 21 by using data C1 that is a parameter to correct respective variations in sensitivity per pixel of the imaging device 21 caused by sensitivity of each pixel of the imaging device 21. Moreover, the image correcting unit 333 subjects the image imaged by the imaging device 21 to white defect correction or black defect correction by using data A and data B, which are non-compressed data read from the storage unit 23.

Other Configurations

The light source unit 4 is a light source that generates illumination light or excitation light emitted from a distal end of the endoscope 2. The light source unit 4 outputs illumination light or excitation light according to a control signal from the control unit 31. The light source unit 4 includes, for example, a white light emitting diode (LED) that emits white illumination light. The light source unit 4 may include special observation-light source that emits special observation light.

The display unit 5 has a function of receiving an image signal generated by the processor 3 through a video cable from the processor 3 and of displaying it. The display unit 5 includes a display such as a liquid crystal display, and an organic electroluminescence (EL) display.

As described above, in the endoscope system 1 according to the present embodiment, data C1 is compressed. Accordingly, increase of volume of data to be transferred from the endoscope 2 to the processor 3 can be suppressed, and increase of data transfer time from the endoscope 2 to the processor 3 can be suppressed.

First Modification

Figure 3:
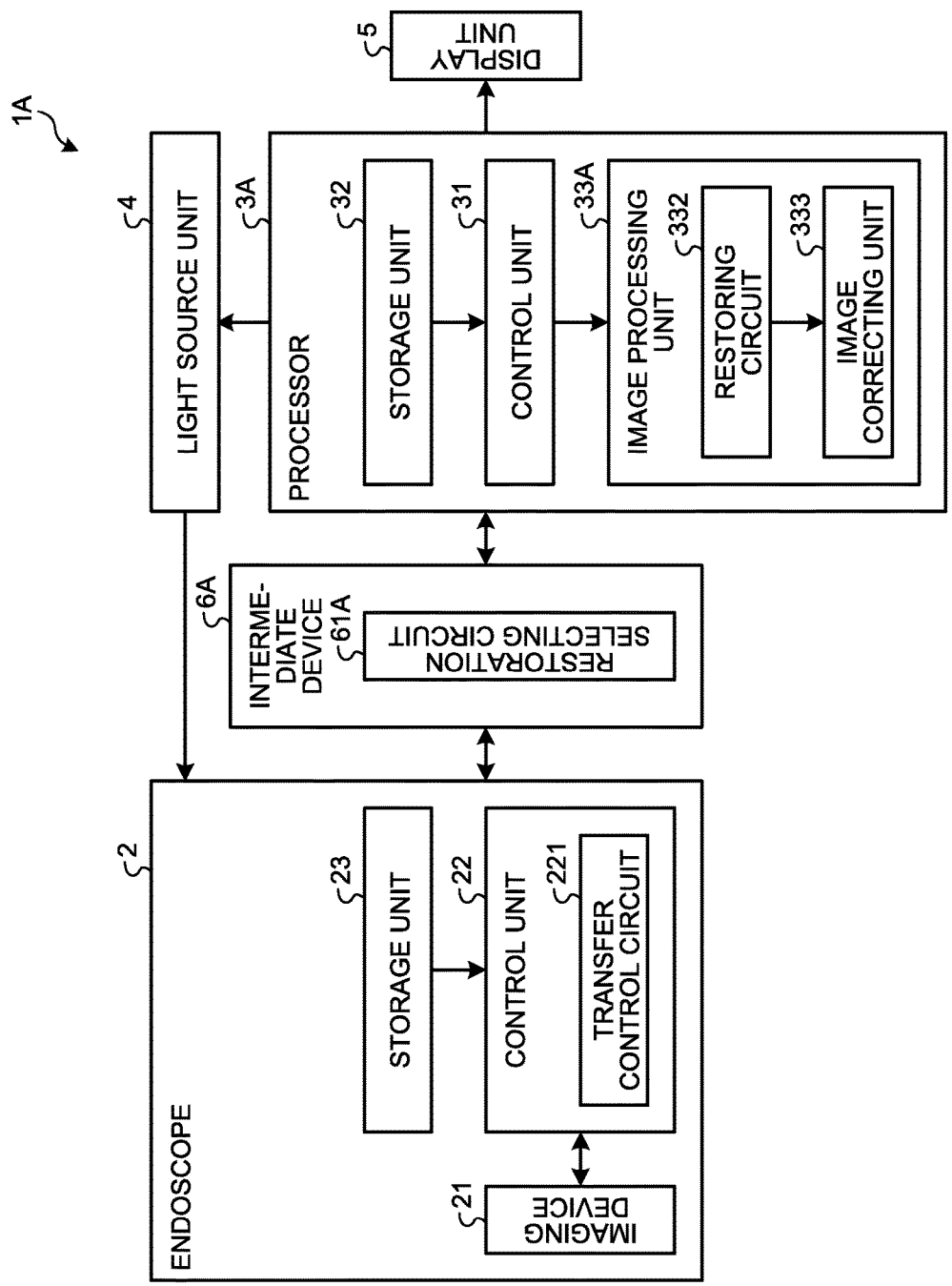
FIG. 3 is a schematic diagram illustrating a configuration of an endoscope system according to a first modification of the embodiment of the disclosure.

FIG. 3 is a schematic diagram illustrating a configuration of an endoscope system according to a first modification of the embodiment of the disclosure. As illustrated in FIG. 3, in an endoscope system 1A, an image processing unit 33A of a processor 3A has no restoration selecting circuit. On the other hand, an intermediate device 6A arranged between the endoscope 2 and the processor 3A includes a restoration selecting circuit 61A. As described, a configuration in which a processor has no restoration selecting circuit may also be applicable.

Second Modification

Figure 4:
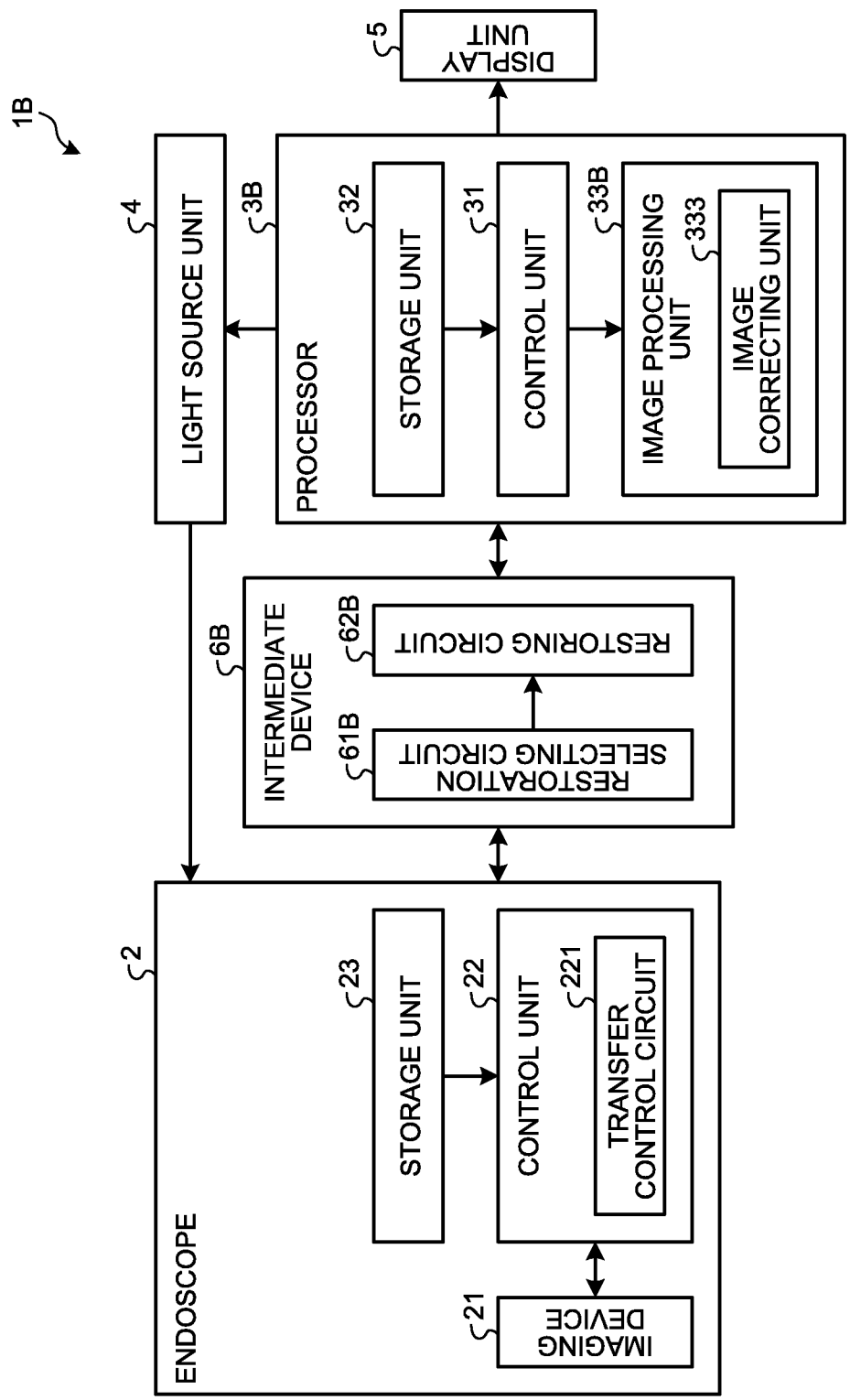
FIG. 4 is a schematic diagram illustrating a configuration of an endoscope system according to a second modification of the embodiment of the disclosure.

FIG. 4 is a schematic diagram illustrating a configuration of an endoscope system according to a second modification of the embodiment of the disclosure. As illustrated in FIG. 4, in an endoscope system 1B, an image processing unit 33B of a processor 3B has no restoration selecting circuit nor restoring circuit. ON the other hand, an intermediate device 6B arranged between the endoscope and the processor 3B includes a restoration selecting circuit 61B and a restoring circuit 62B. As described, a configuration in which a processor has no restoration selecting circuit nor restoring circuit may also be applicable.

In the embodiment, it is configured such that only part of data (data C1) is compressed, but all of non-compressed data may be compressed to be stored in the storage unit 23. In this case, a restoration selecting circuit becomes unnecessary, and all of compressed data read from the storage unit 23 by a restoring circuit are restored to non-compressed data.

Moreover, in the embodiment, an endoscope system in which an endoscope having a flexible insertion portion is adopted has been described as an imaging system, but it may be an endoscope system in which an endoscope having a rigid insertion portion is adopted also. Furthermore, as an imaging apparatus, not limited to an endoscope in which an imaging device is provided at a distal end of an insertion portion, a configuration in which an eyepiece camera head of an optical endoscope, such as a fiberscope and an optical telescope, is connected may be applied. Moreover, as an imaging system, not limited to a medical endoscope system, it is applicable to an industrial endoscope system also.

According to the disclosure, it is possible to provide an imaging system and an imaging apparatus in which increase of data transfer time is suppressed even when a volume of data transferred from the imaging apparatus to a processor increases.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
an endoscope having an image sensor configured to image an inside of a subject;
a processor configured to perform predetermined image processing on a video signal that is imaged by the image sensor;
a storage that is provided in the endoscope, the storage being configured to store compressed data obtained by compressing data volume of first non-compressed data that is used for correction of an image imaged by the image sensor;
a restoring circuit configured to read the compressed data from the storage to restore the compressed data to the first non-compressed data when data is transferred from the endoscope to the processor; and
an image correcting circuit that is provided in the endoscope, the image correcting circuit being configured to correct the image imaged by the image sensor by using the first non-compressed data restored by the restoring circuit.

2. The endoscope system according to claim 1, wherein the storage is configured to store second non-compressed data that is different from the first non-compressed data used for correction of the image imaged by the image sensor,
the endoscope system further comprising
a restoration selecting circuit configured to read the compressed data and the second non-compressed data from the storage to output the compressed data selectively to the restoring circuit when data is transferred from the endoscope to the processor.

3. The endoscope system according to claim 2, wherein the image correcting circuit is configured to correct the image imaged by the image sensor by using the first non-compressed data restored by the restoring circuit and the second non-compressed data read from the storage.

4. The endoscope system according to claim 1, wherein the compressed data is data obtained by compressing the first non-compressed data by using any one of relative value and difference value calculated from a value corresponding to each pixel of the first non-compressed data, and
the restoring circuit is configured to restore the compressed data to an absolute value corresponding to each pixel.

5. The endoscope system according to claim 1, wherein the first non-compressed data is a parameter that is used when different correction is performed per pixel with respect to all pixels of the image imaged by the image sensor.

6. The endoscope system according to claim 1, wherein the first non-compressed data is a parameter to correct respective variations in sensitivity per pixel of the image sensor.

7. The endoscope system according to claim 1, wherein the restoring circuit is provided in the processor.

8. The endoscope system according to claim 2, wherein the restoration selecting circuit is provided in an intermediate device arranged between the endoscope and the processor.

9. The endoscope system according to claim 2, wherein the restoring circuit and the restoration selecting circuit are provided in an intermediate device arranged between the endoscope and the processor.

* * * * *